(12) United States Patent
Malek (10) Patent No.: US 8,187,304 B2
(45) Date of Patent: May 29, 2012

(54) FACET FUSION SYSTEM

(76) Inventor: Michel H. Malek, Chicago, IL (US)

( * ) Notice: Subject to any disclaimer, the term of this patent is extended or adjusted under 35 U.S.C. 154(b) by 687 days.

(21) Appl. No.: 12/267,950

(22) Filed: Nov. 10, 2008

(65) Prior Publication Data

US 2010/0121378 A1    May 13, 2010

(51) Int. Cl.
*A61B 17/70* (2006.01)
(52) U.S. Cl. ............ 606/247; 606/249; 623/17.16
(58) Field of Classification Search .......... 606/246–249; 623/17.11, 17.16, 17.12–17.15
See application file for complete search history.

(56) References Cited

U.S. PATENT DOCUMENTS

| | | | |
|---|---|---|---|
| 4,011,602 A | 3/1977 | Rybicki et al. |
| 4,349,921 A | 9/1982 | Kuntz |
| 4,401,112 A | 8/1983 | Resaian |
| 4,643,178 A | 2/1987 | Nastari et al. |
| 4,657,550 A | 4/1987 | Daher |
| 4,743,256 A | 5/1988 | Brantigan |
| 4,743,260 A | 5/1988 | Burton |
| 4,759,766 A | 7/1988 | Büettner-Janz et al. |
| 4,759,769 A | 7/1988 | Hedman et al. |
| 4,863,476 A | 9/1989 | Shepperd |
| 4,946,378 A | 8/1990 | Hirayama et al. |
| 4,946,458 A | 8/1990 | Harms et al. |
| 4,997,432 A | 3/1991 | Keller |
| 5,024,670 A | 6/1991 | Smith et al. |
| 5,084,048 A | 1/1992 | Jacob et al. |
| 5,092,866 A | 3/1992 | Breard et al. |
| 5,122,130 A | 6/1992 | Keller |
| 5,246,458 A | 9/1993 | Graham |
| 5,258,031 A | 11/1993 | Salib et al. |
| 5,261,911 A | 11/1993 | Carl |
| 5,282,863 A | 2/1994 | Burton |
| 5,306,310 A | 4/1994 | Siebels |
| 5,314,477 A | 5/1994 | Marnay |
| 5,314,478 A | 5/1994 | Oka et al. |
| 5,336,223 A | 8/1994 | Rogers |
| 5,352,224 A | 10/1994 | Westermann |
| 5,375,823 A | 12/1994 | Navas |
| 5,380,324 A | 1/1995 | Müller et al. |
| 5,380,328 A | 1/1995 | Morgan |
| 5,401,269 A | 3/1995 | Büttner-Janz et al. |
| 5,415,659 A | 5/1995 | Lee et al. |

(Continued)

FOREIGN PATENT DOCUMENTS

DE    22 63 842 A    7/1974

(Continued)

OTHER PUBLICATIONS

The International Search Report and Written Opinion for PCT/US2004/032116 mailed on Feb. 16, 2005, 12 pages.

(Continued)

*Primary Examiner* — Eduardo C Robert
*Assistant Examiner* — Jan Christopher Merene
(74) *Attorney, Agent, or Firm* — Foley & Lardner LLP (57) ABSTRACT

A device including a side wall defining an inner space; a lock mechanism; a pivot post; and a securement post where the device is a facet joint fusion cage; and a facet joint distractor is capable of engaging the lock mechanism via a lock and key arrangement. A method of using such a device includes positioning the facet fusion cage in the facet joint of a patient in need of facet joint fusion; and moving the securement post to a locked position.

10 Claims, 5 Drawing Sheets

U.S. PATENT DOCUMENTS

| | | | |
|---|---|---|---|
| 5,437,671 A | 8/1995 | Lozier et al. | |
| 5,458,641 A | 10/1995 | Ramirez Jimenez | |
| 5,496,318 A | 3/1996 | Howland et al. | |
| 5,534,029 A | 7/1996 | Shima | |
| 5,536,124 A | 7/1996 | Silva | |
| 5,540,688 A | 7/1996 | Navas | |
| 5,556,431 A | 9/1996 | Büttner-Janz | |
| 5,562,738 A | 10/1996 | Boyd et al. | |
| 5,563,124 A | 10/1996 | Damien et al. | |
| 5,591,166 A | 1/1997 | Bernhardt et al. | |
| 5,607,425 A | 3/1997 | Rogozinski | |
| 5,628,740 A | 5/1997 | Mullane | |
| 5,645,596 A | 7/1997 | Kim et al. | |
| 5,649,925 A | 7/1997 | Barbera Alacreu | |
| 5,672,175 A | 9/1997 | Martin | |
| 5,688,275 A | 11/1997 | Koros et al. | |
| 5,702,453 A | 12/1997 | Rabbe et al. | |
| 5,702,455 A | 12/1997 | Saggar | |
| 5,713,899 A | 2/1998 | Marnay et al. | |
| 5,725,582 A | 3/1998 | Bevan et al. | |
| 5,776,198 A | 7/1998 | Rabbe et al. | |
| 5,836,948 A | 11/1998 | Zucherman et al. | |
| 5,888,226 A | 3/1999 | Rogozinski | |
| 5,893,889 A | 4/1999 | Harrington | |
| 5,951,553 A | 9/1999 | Betz et al. | |
| 5,989,290 A | 11/1999 | Biedermann et al. | |
| 6,019,792 A | 2/2000 | Cauthen | |
| 6,030,389 A | 2/2000 | Wagner et al. | |
| 6,063,121 A | 5/2000 | Xavier et al. | |
| 6,074,390 A | 6/2000 | Zucherman et al. | |
| 6,083,224 A | 7/2000 | Gertzbein et al. | |
| 6,113,637 A | 9/2000 | Gill et al. | |
| 6,139,579 A | 10/2000 | Steffee et al. | |
| 6,146,421 A | 11/2000 | Gordon et al. | |
| 6,179,873 B1 * | 1/2001 | Zientek | 623/17.11 |
| 6,179,874 B1 | 1/2001 | Cauthen | |
| 6,214,012 B1 | 4/2001 | Karpman et al. | |
| 6,217,578 B1 | 4/2001 | Crozet et al. | |
| 6,228,118 B1 | 5/2001 | Gordon | |
| 6,241,730 B1 | 6/2001 | Alby | |
| 6,293,949 B1 | 9/2001 | Justis et al. | |
| 6,296,644 B1 | 10/2001 | Saurat et al. | |
| 6,296,664 B1 | 10/2001 | Middleton | |
| 6,315,797 B1 | 11/2001 | Middleton | |
| 6,368,350 B1 | 4/2002 | Erickson et al. | |
| 6,375,682 B1 | 4/2002 | Fleischmann et al. | |
| 6,375,683 B1 | 4/2002 | Crozet et al. | |
| 6,395,034 B1 | 5/2002 | Suddaby | |
| 6,402,750 B1 | 6/2002 | Atkinson et al. | |
| 6,419,703 B1 | 7/2002 | Fallin et al. | |
| 6,454,807 B1 | 9/2002 | Jackson | |
| 6,478,800 B1 | 11/2002 | Fraser et al. | |
| 6,500,178 B2 | 12/2002 | Zucherman et al. | |
| 6,517,580 B1 | 2/2003 | Ramadan et al. | |
| 6,520,990 B1 | 2/2003 | Ray | |
| 6,540,785 B1 | 4/2003 | Gill et al. | |
| 6,554,831 B1 | 4/2003 | Rivard et al. | |
| 6,565,605 B2 | 5/2003 | Goble et al. | |
| 6,579,319 B2 | 6/2003 | Goble et al. | |
| 6,579,320 B1 | 6/2003 | Gauchet et al. | |
| 6,582,466 B1 | 6/2003 | Gauchet | |
| 6,582,468 B1 | 6/2003 | Gauchet | |
| 6,585,769 B1 | 7/2003 | Muhanna et al. | |
| 6,607,558 B2 | 8/2003 | Kuras | |
| 6,616,669 B2 | 9/2003 | Ogilvie et al. | |
| 6,626,905 B1 | 9/2003 | Schmiel et al. | |
| 6,626,908 B2 | 9/2003 | Cooper et al. | |
| 6,652,585 B2 | 11/2003 | Lange | |
| 6,685,742 B1 | 2/2004 | Jackson | |
| 6,695,842 B2 | 2/2004 | Zucherman et al. | |
| 6,730,126 B2 | 5/2004 | Boehm, et al. | |
| 6,752,831 B2 | 6/2004 | Sybert et al. | |
| 6,761,720 B1 | 7/2004 | Senegas | |
| 6,764,515 B2 | 7/2004 | Ralph et al. | |
| 6,767,367 B1 * | 7/2004 | Michelson | 623/17.16 |
| 6,770,096 B2 * | 8/2004 | Bolger et al. | 623/17.16 |
| 6,835,205 B2 | 12/2004 | Atkinson et al. | |
| 6,852,128 B2 | 2/2005 | Lange | |
| 6,902,566 B2 | 6/2005 | Zucherman et al. | |
| 6,946,000 B2 | 9/2005 | Senegas et al. | |
| 6,966,910 B2 | 11/2005 | Ritland | |
| 6,966,931 B2 | 11/2005 | Huang | |
| 6,989,011 B2 | 1/2006 | Paul et al. | |
| 7,022,138 B2 | 4/2006 | Mashbum | |
| 7,025,787 B2 | 4/2006 | Bryan et al. | |
| 7,041,138 B2 | 5/2006 | Lange | |
| 7,044,970 B2 | 5/2006 | Errico et al. | |
| 7,056,343 B2 | 6/2006 | Schafer et al. | |
| 7,101,375 B2 | 9/2006 | Zucherman et al. | |
| 7,147,665 B1 | 12/2006 | Bryan et al. | |
| 7,175,623 B2 | 2/2007 | Thramann et al. | |
| 7,186,256 B2 | 3/2007 | Michelson | |
| 7,201,751 B2 | 4/2007 | Zucherman et al. | |
| 7,255,713 B2 | 8/2007 | Malek | |
| 7,282,064 B2 | 10/2007 | Chin | |
| 7,318,825 B2 | 1/2008 | Butler et al. | |
| 7,402,176 B2 | 7/2008 | Malek | |
| 2001/0016773 A1 | 8/2001 | Serhan et al. | |
| 2001/0029375 A1 | 10/2001 | Betz et al. | |
| 2001/0032020 A1 | 10/2001 | Besselink | |
| 2001/0037111 A1 | 11/2001 | Dixon et al. | |
| 2001/0051829 A1 | 12/2001 | Middleton | |
| 2002/0022888 A1 | 2/2002 | Serhan et al. | |
| 2002/0107574 A1 | 8/2002 | Boehm, Jr. et al. | |
| 2002/0111683 A1 | 8/2002 | Ralph et al. | |
| 2002/0147454 A1 | 10/2002 | Neto | |
| 2003/0009223 A1 | 1/2003 | Fehling et al. | |
| 2003/0009226 A1 | 1/2003 | Graf | |
| 2003/0018390 A1 | 1/2003 | Husson | |
| 2003/0023312 A1 | 1/2003 | Thalgott | |
| 2003/0032958 A1 | 2/2003 | Soubeiran | |
| 2003/0055427 A1 | 3/2003 | Graf | |
| 2003/0100951 A1 | 5/2003 | Serhan et al. | |
| 2003/0149484 A1 * | 8/2003 | Michelson | 623/17.16 |
| 2003/0176861 A1 | 9/2003 | Reed | |
| 2003/0187436 A1 * | 10/2003 | Bolger et al. | 606/61 |
| 2003/0191534 A1 | 10/2003 | Viart et al. | |
| 2003/0229348 A1 | 12/2003 | Sevrain | |
| 2004/0002762 A1 | 1/2004 | Hawkins | |
| 2004/0153156 A1 | 8/2004 | Cohen et al. | |
| 2004/0167626 A1 | 8/2004 | Geremakis et al. | |
| 2005/0004673 A1 * | 1/2005 | Kluger | 623/17.11 |
| 2005/0085910 A1 | 4/2005 | Sweeney | |
| 2005/0113927 A1 | 5/2005 | Malek | |
| 2005/0124993 A1 * | 6/2005 | Chappuis | 606/61 |
| 2005/0131536 A1 * | 6/2005 | Eisermann et al. | 623/17.11 |
| 2005/0143823 A1 | 6/2005 | Boyd et al. | |
| 2005/0165486 A1 | 7/2005 | Trieu | |
| 2005/0209593 A1 | 9/2005 | Kolb | |
| 2005/0209697 A1 | 9/2005 | Paponneau et al. | |
| 2005/0216085 A1 * | 9/2005 | Michelson | 623/17.11 |
| 2005/0234425 A1 | 10/2005 | Miller et al. | |
| 2006/0036243 A1 | 2/2006 | Sasso et al. | |
| 2006/0064099 A1 * | 3/2006 | Pavlov et al. | 606/72 |
| 2006/0079895 A1 | 4/2006 | McLeer | |
| 2006/0106381 A1 | 5/2006 | Ferree et al. | |
| 2006/0161154 A1 | 7/2006 | McAfee | |
| 2006/0190081 A1 * | 8/2006 | Kraus et al. | 623/17.11 |
| 2006/0200140 A1 | 9/2006 | Lange | |
| 2006/0224223 A1 | 10/2006 | Podhajsky et al. | |
| 2007/0010813 A1 | 1/2007 | Zucherman et al. | |
| 2007/0083265 A1 * | 4/2007 | Malone | 623/17.11 |
| 2007/0112299 A1 | 5/2007 | Smit et al. | |
| 2007/0173937 A1 | 7/2007 | Khalili | |
| 2007/0250166 A1 * | 10/2007 | McKay | 623/17.11 |
| 2007/0270828 A1 | 11/2007 | Bruneau et al. | |
| 2008/0027444 A1 | 1/2008 | Malek | |
| 2008/0255666 A1 * | 10/2008 | Fisher et al. | 623/17.16 |
| 2009/0062919 A1 | 3/2009 | Malek | |
| 2009/0099601 A1 * | 4/2009 | Aferzon et al. | 606/246 |
| 2009/0177233 A1 | 7/2009 | Malek | |
| 2009/0204149 A1 | 8/2009 | Malek | |
| 2009/0287118 A1 | 11/2009 | Malek | |
| 2010/0121378 A1 | 5/2010 | Malek | |
| 2010/0160964 A1 | 6/2010 | Malek | |
| 2011/0054530 A1 * | 3/2011 | Lins | 606/247 |

FOREIGN PATENT DOCUMENTS

| | | |
|---|---|---|
| DE | 30 23 353 A1 | 4/1981 |
| EP | 0 176 728 A | 4/1986 |
| EP | 0 560 140 B1 | 9/1993 |
| EP | 0 560 141 A | 9/1993 |
| EP | 0 566 810 B1 | 10/1993 |
| FR | 2 694 882 A | 2/1994 |
| FR | 2801782 | 12/1999 |
| FR | 2 805 985 | 9/2001 |
| WO | WO 94/04100 | 3/1994 |
| WO | WO 95/26697 | 10/1995 |
| WO | WO 01/06939 | 2/2001 |
| WO | WO 02/24087 | 3/2002 |
| WO | WO 2008/014337 | 1/2008 |
| WO | WO 2009/088746 | 7/2009 |
| WO | WO 2009/100117 | 8/2009 |

OTHER PUBLICATIONS

"Anatomic Facet Replacement System (AFRS™)," *Natural Motion*; published by Facet Solutions, Inc.; http://www.facetsolutions.com/Device.html on or before Nov. 2, 2007, 1 page.

* cited by examiner

FACET FUSION SYSTEM

BACKGROUND

Skeletal structures are comprised of bone, i.e., mineralized osseous tissue, and adjoining structures which include cartilage, among other elements. The spinal column is a highly complex skeletal structure which houses and protects critical elements of the nervous system. Although the spinal column is elaborate, it is a highly flexible structure capable of a wide range of motion. The human spine is composed of thirty-three vertebrae and their adjoining structures. Twenty-four of the thirty-six vertebrae are distinct bones capable of individual movement which are connected via facet joints. Facet joints allow the spine to move in every direction and maintain its flexibility. However, various diseases such as arthritis, degenerative disc disease, developmental abnormalities, trauma, chronic stress, and tumors, can result in spinal or facet pathologies which limit a patient's range of motion. Accordingly, the spine may require artificial support or stabilization at some point in a patient's life. One method of stabilizing the spine is by fusing facet joints. Facet joint fusion can reduce or eliminate pain and complications associated with degenerating facet joints.

While known devices for facet fusion are effective in certain applications, there remains a need for facet joint implants that do not require large incisions for implantation, relieve localized stress on adjacent vertebral end-plates, and can prevent migration and retropulsion within the spinal column.

SUMMARY

In one aspect, a device includes a side wall having an interior surface and an exterior surface, wherein the interior surface defines an inner space and the exterior surface defines a distractor tip engagement mechanism configured to engage a facet joint distractor; and a securement post having a first end and a second end opposite the first end, where the securement post is secured within the inner space and configured to pivot from an unsecured position to a secured position; where the device is a facet joint fusion cage. Such devices are to be inserted in a facet joint to aid in, or facilitate the fusion of the facet joint. In some embodiments, the device also includes one or more anti-retropulsion spikes on an exterior surface of the facet joint fusion cage.

In some embodiments, the device includes a pivot post secured to the interior surface of the side wall, where the securement post is mounted to and configured to pivot about, or with, the pivot post. In other embodiments, the distractor tip engagement mechanism is configured to engage the tip of a facet joint distractor. In other embodiments, in the secured position, one, or both, of the first end and the second end, are configured to extend beyond the side wall.

In some embodiments, the devices includes one or more buttress plates. In other embodiments, device contains bone graft material or bone substitute material. In some such embodiments, the bone graft material or bone substitute material is bone graft, allograft bone, demineralized bone material, ceramic, coral, collagen/ceramic composite, bone morphogentic protein, or a combination of any two or more. In some embodiments, the bone graft material or bone substitute material is a source of osteogenesis, a fusion promoting substance, a bone growth promoting material, a bone, a bone derived substances, a demineralized bone matrix, a mineralizing protein, a plasma spray coating, an ossifying protein, a bone morphogenetic protein, hydroxyapatite, genes coding for the production of bone, substances other than bone, or a mixture of any two or more thereof. In yet other embodiments, the device one or more fenestrations through the side wall.

In another aspect, an expandable facet joint fusion cage includes an expandable cage, which includes a first part; including a first side wall including an interior surface that defines a first inner space, a first exterior surface, and an edge, wherein the edge further comprises a channel; a second part including a second side wall having an interior surface that defines a second inner space and a second exterior surface; and a securement post having a first end and a second end opposite the first end, where the securement post is secured within the expandable cage and configured to pivot from an unsecured position to a secured position; where the second side wall is configured to slidably nest within the channel; and at least one of the exterior surface of the first side wall or the exterior surface of the third side wall defines a distractor tip engagement mechanism.

In some embodiments, the expandable facet joint fusion cage includes anti-retropulsion spikes on the exterior surfaces of the first part, the second part, or both the first part and the second part. In other embodiments, the device includes a pivot post secured to the interior surface of the first side wall, or the interior surface of the second side wall, where the securement post is mounted to the pivot post and is configured to pivot about, or with, the pivot post. In yet other embodiments, the distractor tip engagement mechanism is configured to engage the tip of a facet joint distractor.

In some embodiments of the expandable facet joint fusion cage, in the secured position, the first end is configured to extend beyond the first side wall, or the second end is configured to extend beyond the third side wall, or both the first end is configured to extend beyond the first side wall and the second end is configure to extend beyond the second side wall. In some embodiments, the expandable facet joint fusion cage includes one or more buttress plates attached to the first part, the second part, or both the first and second parts. In other embodiments, the expandable facet joint fusion cage contains bone graft material or bone substitute material. The expandable facet joint fusion cage may also have one or more fenestrations through the side wall.

In another aspect, a method of using the facet joint fusion cage is provided including positioning the facet fusion cage in a facet joint of a patient in need of a facet joint fusion; and pivoting the securement post from a first to a secured position, where in the secured position one, or both, of the first end and the second end, are configured to extend beyond the side wall. Where the facet joint fusion cage includes buttress plates, the method may include securing the buttress plates to the bone or tissue surrounding the facet joint.

In another aspect, a method of using the expandable facet joint fusion cage is provided including positioning the expandable facet fusion cage in a facet joint of a patient in need of facet joint fusion, where the facet fusion cage is in a collapsed state; expanding the expandable facet fusion cage to an expanded state; and moving the securement post to a secured position. The moving and expanding may be in any order. Where the expandable facet joint fusion cage includes buttress plates, the method may include securing the buttress plates to the bone or tissue surrounding the facet joint.

In another aspect, a facet joint fusion kit includes a facet joint fusion cage, an insertable guide; a dilator; a facet joint spreader; and a rasp.

In another aspect, a method of using the facet joint fusion kit includes accessing a facet joint of a patient's spinal column; inserting the insertable guide into the facet joint; dilating a facet joint with the dialator; inserting the facet joint spreader within the facet joint; rotating the facet joint spreader 90° to distract the facet joint; deploying the rasp over the facet joint spreader; decorticating an interior surface of the facet joint with the rasp; removing the rasp; inserting the fusion cage attached to a tip of a distractor into the facet joint; disengaging the detachable distractor tip from the fusion cage; and pivoting the securement post to a secured position. In some embodiments, accessing a patient's spinal column includes using an endoscopic or blinded surgical approach. In other embodiments, the insertable guide facilitates the directional positioning of: the dilator; the distractor; the facet joint spreader; the rasp; and the facet joint fusion cage. In other embodiments, the method also includes positioning the insertable guide using a paraspinal fluoro-guide. In other embodiments, the method also includes positioning the insertable guide unilaterally or bilaterally along the spinal column.

DETAILED DESCRIPTION

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented here.

Facet fusion cages are provided, as well as methods for the use of such devices. and methods for the system are provided. In general, the facet fusion cages are intended for use in fusing together various parts of a facet joint, as found in the spinal structure of an animal, including humans. The facet fusion cages have built-in securement devices that allow a surgeon to readily secure the cage within the facet joint such that it does not slip or move, post-insertion.

In one aspect, a facet fusion cage is provided including a side wall having an interior surface and an exterior surface, where the interior surface defines an inner space and the exterior surface defines a distractor tip engagement mechanism configured to engage a facet joint distractor; and a securement post having a first end and a second end opposite the first end, where the securement post is secured within the inner space and configured to pivot from an unsecured position to a secured position.

Figure 1:
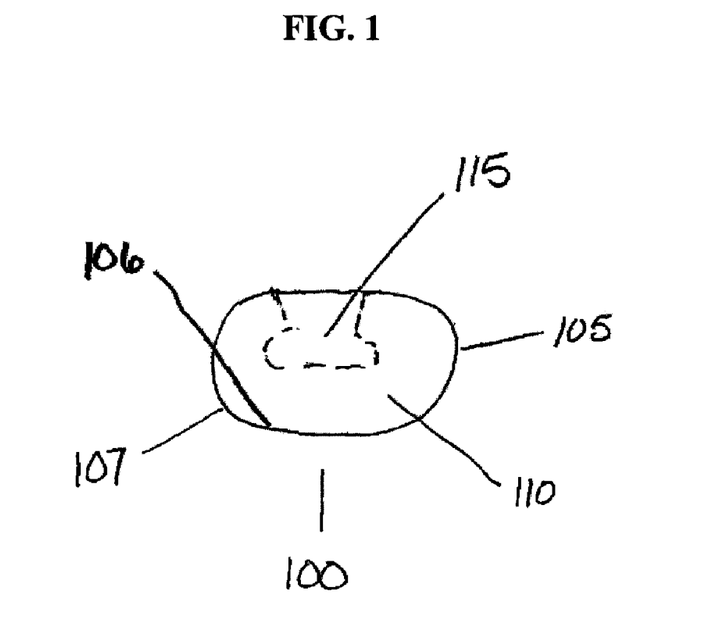
FIG. 1 is a top, plain view of a facet fusion cage showing a distractor tip engagement mechanism, according to one embodiment.

Referring to the figures, FIG. 1 is a top view illustration of a facet joint fusion cage 100. The fusion cage 100 includes a side wall 105 having an interior surface 106 and an exterior surface 107. The interior surface 106 defines an interior space 110. Also included in the cage is a distractor tip engagement mechanism 115. The distractor tip engagement mechanism 115 is capable of engagement by a tip of a facet joint distractor via threading, a bayonet style connection, a lock and key type mechanism as illustrated in FIG. 1, or by other such attachment means. The engagement mechanism may not be so limited to only facet joint distractor tips. The function of the facet joint distractor is to have a handle that attaches to the facet joint fusion cage for insertion and placement of the cage within a facet joint. Therefore a rod or other such device that can attach to the facet joint fusion cage is understood to function similarly to the facet joint distractor.

Figure 5:
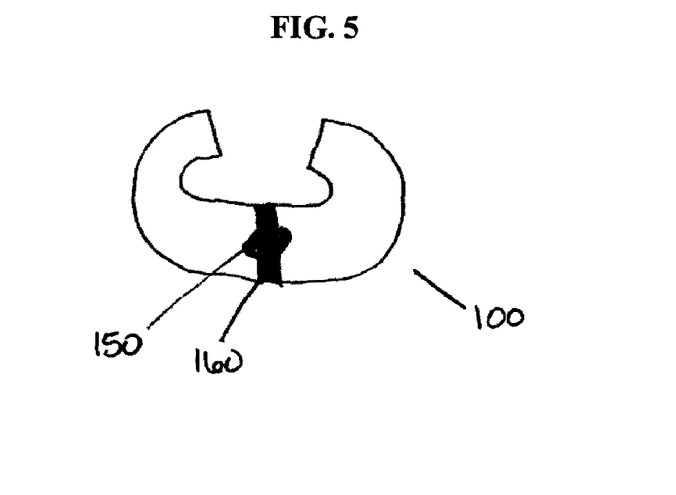
FIG. 5 is a top, cross-sectional view of a facet fusion cage showing a pivot post and a securement post in a secured state, according to one embodiment.
Figure 6:
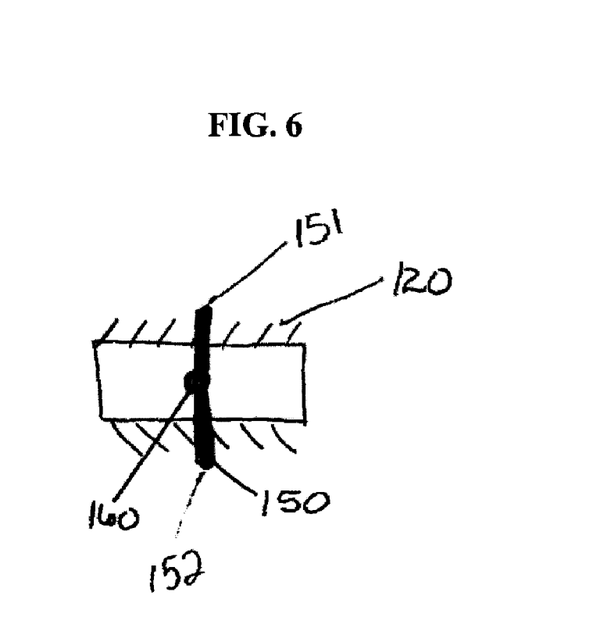
FIG. 6 is a side, cross-sectional view of a facet fusion cage showing a pivot post and a securement post in a secured state, according to one embodiment.

Also included in the facet joint fusion cage 100 are a securement post 150 and a pivot post 160, as illustrated in FIGS. 3, 4, 5, and 6. The pivot post 160 is secured to the interior surface 106 of the side wall 105, and the securement post 150 is associated with the pivot post 160. In some embodiments, the pivot post 160 and the securement post 150 are arranged orthogonally to one another. The pivot post 160 may be secured to the interior surface 106 of the side wall 105 rigidly, in that the securement post 150 pivots about the pivot post 160. Alternatively, the pivot post 160 is pivotally secured to the side wall 105 and the securement post 150 is rigidly mounted on the pivot post 160. The result is such that the securement post 150 is capable of being pivoted from an unsecured state (FIGS. 3 and 4) to a secured state (FIGS. 5 and 6). In some embodiments where the pivot post 160 is pivotally secured to the side wall 105, a portion of the pitvot post 160 extends beyond the side wall 105 such that it is configured to be engaged by a tool or other device to turn the securement post 150 to a secured state.

As used herein, "unsecured state" refers to the orientation of the securement post 150 within the interior space 110 of the facet joint fusion cage 100. As used herein, a "secured state" refer to the orientation of a first end 151 of the securement post 150 and a second end 152 of the securement post 150, opposite to the first end 151, as being capable of extending beyond the exterior surface 107 of the side wall 105. Thus, in the "secured state," the first end 151 and the second end 152 are configured to engage the bone or cartilage surfaces of the two parts of the facet joint; i.e. the superior and inferior surfaces. In one embodiment, one, or both of, the first and second ends 151, 152 extend beyond the exterior surface 107 of the side wall 105. In another embodiment, when the first and second ends 151, 152 are in a secured position, they are within the inner space 110 of the fusion cage 100, however upon receiving pressure from the weight of the patient in which the fusion cage 100 placed, the weight of the patient causes a flex in the fusion cage 100 such that one or both of the ends 151, 152 extend beyond the exterior surface 107 of the side wall 105 and are secured in the inner surface of the facet joint.

In some embodiments, the first end 151 and the second end 152 of the securement post 150 are configured to provide better contact with the bony or cartilage surfaces of the inside of a facet joint. For example, though the ends may be rounded or flat, they may also be pointed, or burred to anchor the facet joint fusion cage securely in the inside surface of the facet joint.

Figure 2:
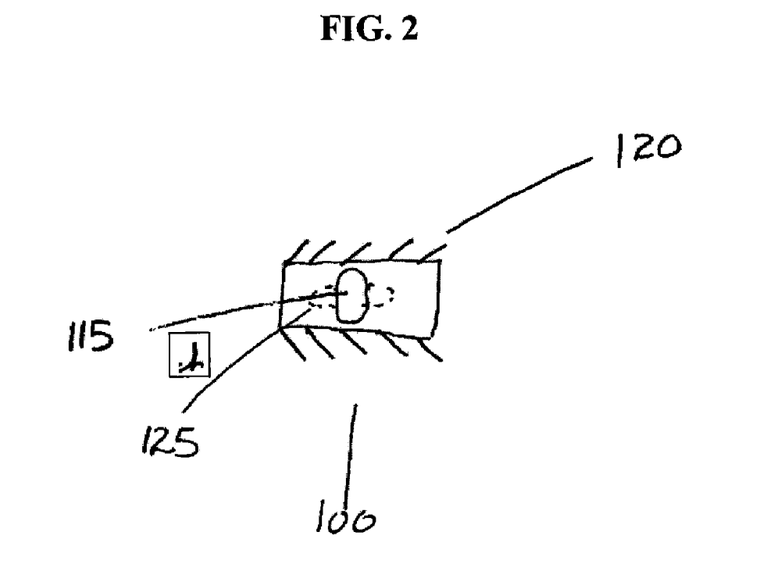
FIG. 2 is a side, plain view of a facet fusion cage showing a distractor tip engagement mechanism, according to one embodiment.
Figure 3:
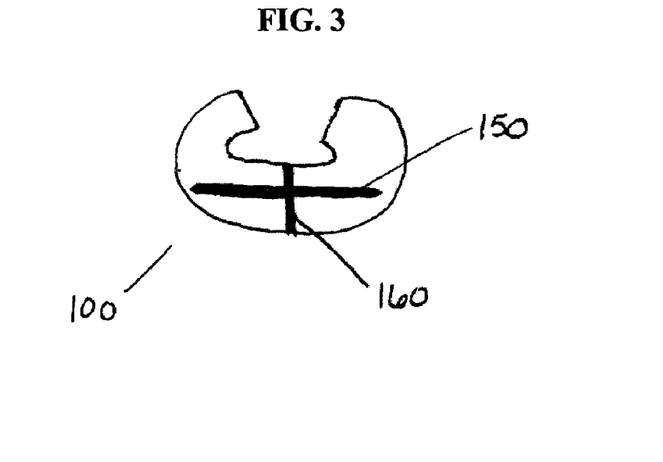
FIG. 3 is a top, cross-sectional view of a facet fusion cage showing a pivot post and a securement post in an unsecured state, according to one embodiment.
Figure 4:
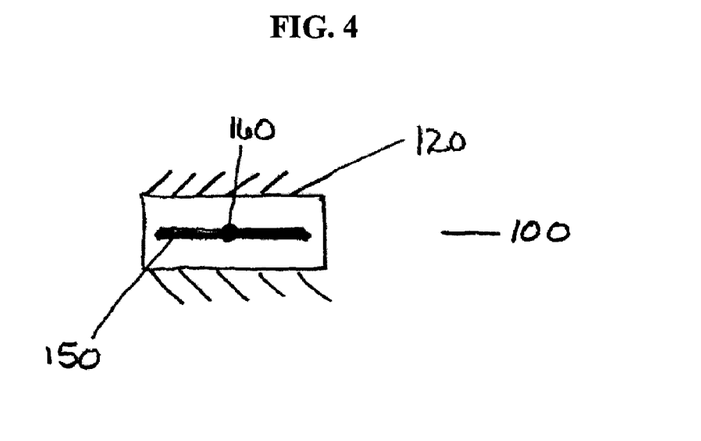
FIG. 4 is a side, cross-sectional view of a facet fusion cage showing a pivot post and a securement post in an unsecured state, according to one embodiment.

In some embodiments, the facet joint fusion cage 100, includes one or more anti-retropulsion spikes 120, on the exterior surface of the fusion cage 100. The one or more anti-retropulsion spikes 120 are oriented such that they prevent, or at least minimize the potential for, ejection of the facet joint fusion cage 100 from a facet joint. The one or more anti-retropulsion spikes 120 may be positioned at the anterior and/or posterior regions of the fusion cage 100, thereby preventing retropulsion of the fusion cage from a facet joint in any direction.

Figure 10:
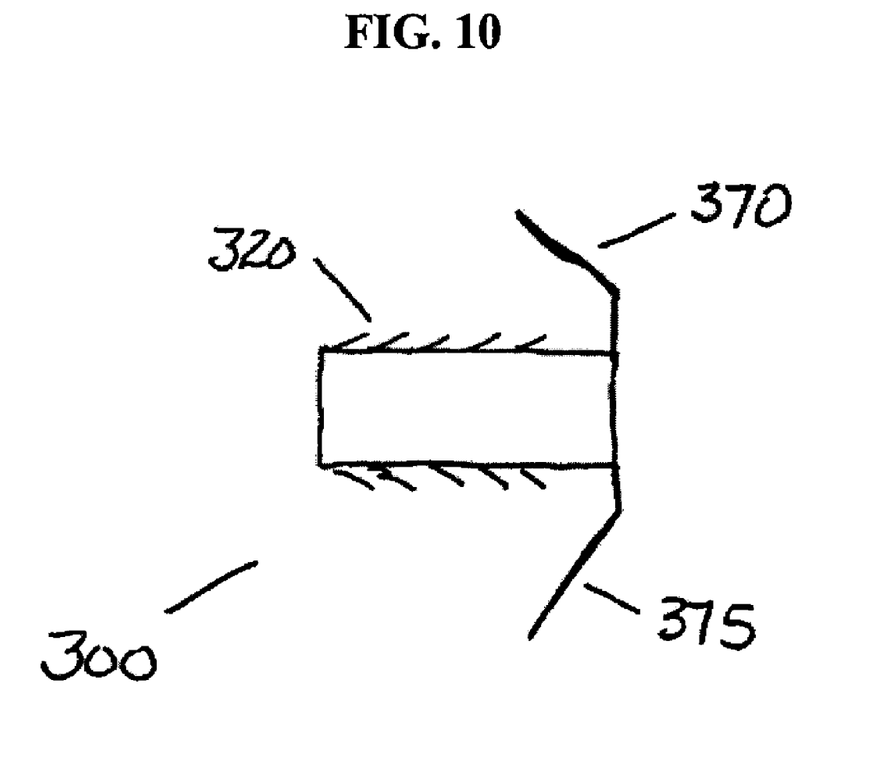
FIG. 10 is a side, plain view of a facet fusion cage with buttress plates, according to one embodiment.

In some embodiments, the facet joint fusion cage 100 includes one or more buttress plates 370. The buttress plates 370 are connected to an exterior surface of the fusion cage 100, or are formed integrally with the fusion case 100 (i.e. all cast or machined from the same piece of material). The buttress plates 370 have holes for receiving a fastener or spikes for engaging bone and/or tissue in the area around the facet joint. For example, the buttress plates 370 may have holes for receiving a bone screw, a nail, a mesh or wire that is wrapped around the facet joint, or other like fastener. Such fasteners as those listed may be uncoated or coated with a porous material to allow for bone ingrowth. Alternatively, for example, the buttress plates have spikes that are pushed into the surrounding bone or tissue to secure the facet joint fusion cage 100 in place.

Figure 7:
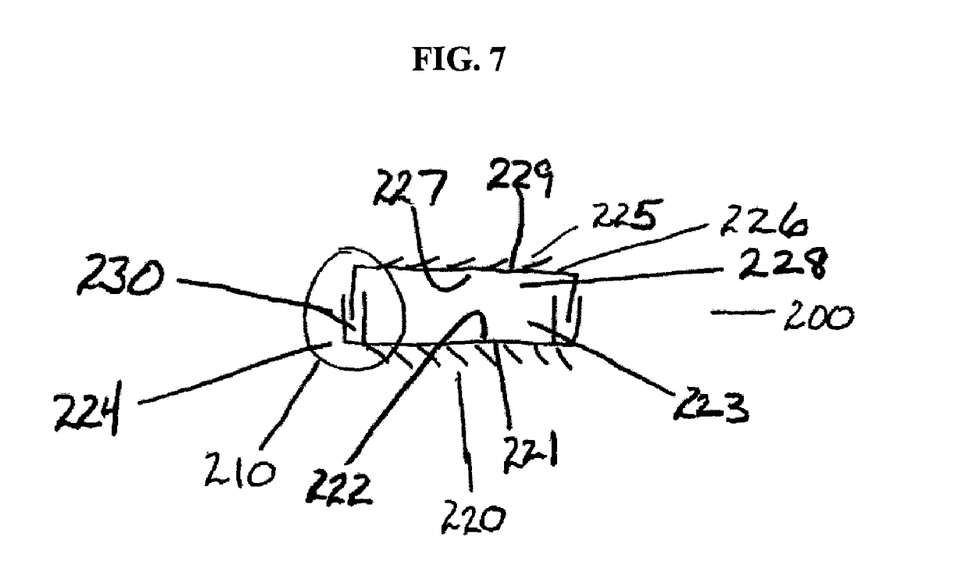
FIG. 7 is a side, cross-sectional view of an expandable facet fusion cage showing a first part with a channel and a second part nested in the channel, according to one embodiment.
Figure 8:
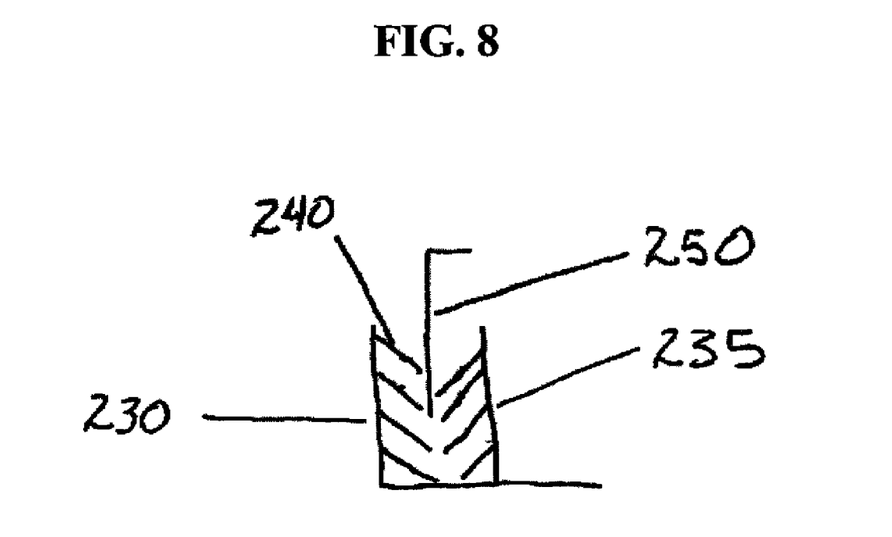
FIG. 8 is a detailed, cross-sectional view of the facet fusion cage and a first part with a channel and a second part nested in the channel generally shown in FIG. 7.
Figure 9:
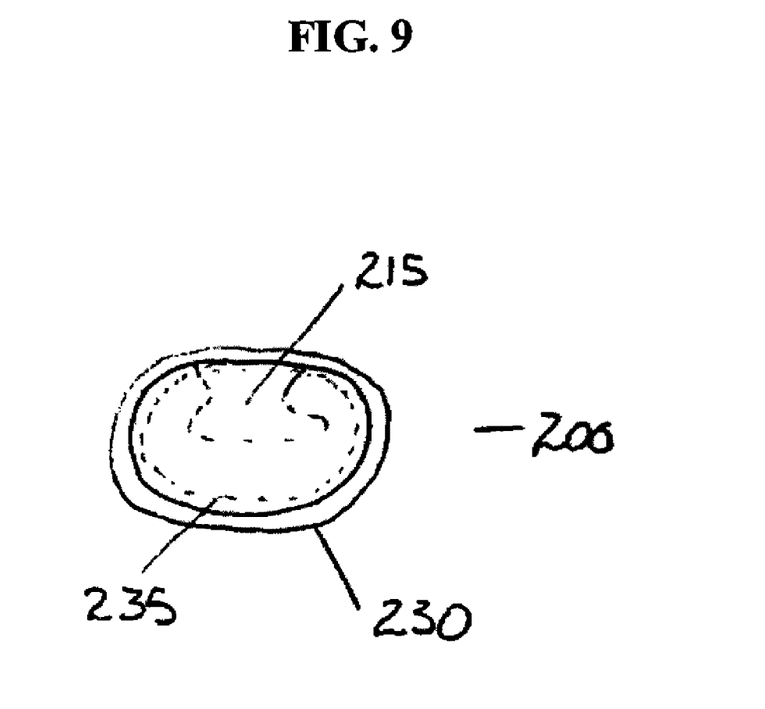
FIG. 9 is a top, plain view of an expandable facet fusion cage showing a first part with a channel and a second part nested in the channel, according to one embodiment.

In another aspect, an expandable facet joint fusion cage 200, is provided. The expandable facet joint fusion cage 200 is similar to the facet joint fusion cage 100, and has a distractor tip engagement mechanism 215, a pivot post (not shown), and a securement post (not shown), except it is expandable. FIGS. 7-9, illustrate an expandable facet joint fusion cage 200. Facet joint fusion cages 200 have a first part 220 and a second part 225, configured to engage one another. The first part 220 has a first side wall 221. The first side wall 221 has an interior surface 222 that defines an interior space 223 and an edge 224 that defines a channel 230. The second part 225 has a second side wall 226 having an interior surface 227, defining an interior space 228, and an exterior surface 229.

In expandable facet joint fusion cages 200, the first part 220 and the second part 225, engage to cooperatively interact to form a single fusion cage device, and interior spaces 223 and 228 become a single interior space when the first and second parts are engaged. To engage, the second side wall 226 nests within the channel 230 of the first part 220. According to one embodiment, the channel 230 is shown in the expanded view of FIG. 8. The channel 230 is configured to receive the second side wall 226 in a tight friction fit so that the expandable fusion cage 200 does not readily collapse under the weight of a patient, but it is amenable to expansion by a surgeon to be accommodated by a facet joint.

In one embodiment, the channel 230 includes one or more friction vanes 240, to provide additional resistance to expansion or collapse of the expandable facet joint fusion cage 200, after the surgeon or other medical profession has set the expansion within the facet joint. The friction vanes 240 provide for a tight, friction fit such that the movement of the first part 220, relative to the second part 225 is restricted. In some embodiments, instead of the one or more anti-expansion vanes 240, inner surfaces of the channel 230 and/or the interior 227 or exterior surface 229 of the second side wall 226 are roughened such that the friction between the channel 230 and the second side wall 226 prevents easy movement of the first part 220 and the second part 225, relative to each other.

Also included in the cage is a distractor tip engagement mechanism 215. The distractor tip engagement mechanism 215 is capable of engagement by a tip of a facet joint distractor via threading, a bayonet style connection, a lock and key type mechanism as illustrated in FIG. 9, or by other such attachment means. The engagement mechanism may not be so limited to only facet joint distractor tips. The function of the facet joint distractor is to have a handle that attaches to the facet joint fusion cage for insertion and placement of the cage within a facet joint. Therefore a rod or other such device that can attach to the facet joint fusion cage is understood to function similarly to the facet joint distractor.

Optionally, the expandable facet fusion cage 200 may include one or more anti-retropulsion spikes 220 on an exterior surface of the first part 220 and/or the second part 225. The one or more anti-retropulsion spikes 220 are oriented such that they prevent, or at least minimize the potential for, ejection of the facet joint fusion cage 200 from a facet joint. The one or more anti-retropulsion spikes 220 may be positioned at the anterior and/or posterior regions of the fusion cage 200, thereby preventing retropulsion of the fusion cage from a facet joint in any direction.

In some embodiments, the expandable facet joint fusion cage 200 includes one or more buttress plates (not illustrated). The buttress plates may be separately prepared parts that are connected to an exterior surface of the fusion cage 200. Alternatively, the buttress plates may be integrally formed, i.e. all cast or machined from the same piece of material, with the fusion case 200. The buttress plates have holes for receiving a fastener or spikes for engaging bone and/or tissue in the area around the facet joint. For example, the buttress plates may have holes for receiving a bone screw, a nail, or other like fastener. One such other like fastener is as described in U.S. Patent Publication No. 2008/0027444. Alternatively, for example, the buttress plates have spikes that are pushed into the surrounding bone or tissue to secure the facet joint fusion cage 200 in place.

In some embodiments, the fusion cages 100, 200 may be flat, have a two- or three-dimensional rounded or oval structure. They may have a squared profile, or a be wedged shape.

In another aspect, the facet joint fusion cages 100, 200 include bone graft material or bone substitute material in the inner space 110, 223, 228. Such materials promote the growth of bone to aid in the fusing of the facet joint in a patient in need of fusion. In some embodiments, the bone graft material or bone substitute material is bone graft, allograft bone, demineralized bone material, ceramic, coral, collagen/ceramic composite, bone morphogentic protein, an osteoconductive material, an osteoinductive materials, or a combination of any two or more. In some such embodiments, the facet joint fusion cages 100, 200 include fenestrations through the fusion cage to connect the inner space 110, 223, 228 to the outside environment in which the cages 100, 200 are located. Such fenestrations allow penetration of bone throughout the cages 100, 200 so they become part of the fusion of the facet joint and are fully incorporated into the growing bone matrix.

As used herein, an "osteoinductive material" refers to any material that is capable of inducing bone formation (i.e., a material having osteogenic properties) when implanted in a body and includes demineralized bone matrix and osteoinductive factors. An "osteoinductive factor" refers to a natural, recombinant or synthetic protein or mixture of proteins which are capable of inducing bone formation. For example, the term osteoinductive factor refers to the materials described as bone growth factors in Damien et al., U.S. Pat. No. 5,563,124. As used herein, "osteoconductive materials" are those that are able to conduct the ingrowth of natural bone when placed against adjacent natural bone. Osteoconductive materials include synthetic ceramic materials, where the osteoconductive ability is a function primarily of the chemistry and also of the geometry (pore size, etc.) in which the materials are manufactured. Some synthetic ceramic materials are resorbable, meaning that they can eventually disappear through normal biochemical processes and be replaced by natural bone. Implantable ceramic structures have been made for this purpose by three-dimensional printing, by molding and by other methods.

In some embodiments, the fusion cages 100, 200 and individual parts of the fusion cages are composed of titanium, titanium alloys, stainless steel, stainless steel alloys, ceramics, biocompatible polymers, and/or carbon-reinforced composites, and the like. The fusion cages 100, 200 may also be include, or be coated with, bone growth materials to facilitate bone growth and attachment. In one embodiment, at least a portion of the fusion cages 100, 200 and parts are made from, or coated with, a porous material that allows for bone ingrowth into the material, helping to secure the fusion cage and/or securing device to the bone. In some embodiments, the porous coating is cobalt chromium alloy, cobalt chromium molybdenum alloy, or porous titanium. In some embodiments, the fusion cages are coated with a fluorescent material to aid in positioning of the devices using a fluoroscope.

In some embodiments, the fusion cage 100, 200 and individual parts of the fusion cages are made from a bioerodable or bioabsorbable material. In such embodiments, the fusion cage 100, 200 provides a structural scaffold upon which the fusion is initiated and propogated, however during the growth of bone and the fusion process the fusion cages may bioerode or bioabsorb to leave only the newly grown bone in the fusion site.

The fusion cage and/or securing device may also be coated or impregnated with materials that promote bone growth such as, but not limited to, any source of osteogenesis, fusion promoting substances, bone growth promoting materials, bone, bone derived substances or products, demineralized bone matrix, mineralizing proteins, plasma spray coatings, ossifying proteins, bone morphogenetic proteins, hydroxyapatite, genes coding for the production of bone, substances other than bone, and bone including, but not limited to, cortical bone. Porous coatings include porous coated alloys such as, but not limited to, cobalt chromium alloy or cobalt chromium molybdenum alloy on a porous layer of beads, or porous titanium.

The fusion cages, screws, and like fasteners may be combined with an antimicrobial material and/or surface treated or coated to be antibacterial and/or antimicrobial, such as for example, by a silver coating. At least one of the plate, screws, fasteners, and/or bone screw locks may be, if so desired, electrified for purposes of stimulating bone growth and contributing to bone fusion.

In another aspect, a method of using the fusion cages are provided. The method includes positioning a facet fusion cage in the facet joint of a patient in need of facet joint fusion; and moving the securement post to a locked position. In some embodiments, where the facet fusion cage is an expandable facet fusion cage, the method includes positioning a collapsed expandable facet fusion cage in the facet joint of a patient in need of facet joint fusion, expanding the expandable facet fusion cage to an expanded state; and moving the securement post to a secured position. The expanding and moving in such embodiments, may be performed in any order. Where the facet fusion cage used in the method includes one or more buttress plates, the methods include securing the one or more buttress plates to the vertebrae, or other bony spinal structure, of a spinal column.

As described above, in such methods the securement post may be moved to a locked position in which one, or both, ends of the securement post protrudes from the fusion cage, or are still within the inner space of the fusion cage. In the case where the one or both of the ends of the secured securement post extend beyond the exterior surface, or surfaces, of the fusion cage, the ends are seated in the tissue or surface of the facet joint to immobilize the fusion cage in the facet joint. In the case where the ends of the secured securement post are within the inner space of the fusion cage, the cage is compressible such that the weight of a patient, into which the fusion cage is deployed, compresses the fusion cage to cause the ends of the securement posts to penetrate or seat in the tissue or surface of the facet joint.

In another aspect, a system is provided, including the facet fusion cages embodied herein. The system may also include, but is not limited to, one or more of an insertable guide, a dilator, an interspinous spreader, a facet joint spreader, and/or a rasp. The insertable guide, dilator, facet joint spreader, and rasp are those items as are known in the art. The insertable guide is used to direct the insertion of other instruments to the facet joint. Thus, in one embodiment, an insertable guide directionally positions the facet fusion system. In another embodiment, the insertable guide is a Stineman pin. In some embodiments, the interspinous space guide is flexible and in other embodiments it is rigid.

In some embodiments, the dilator is a device that may be inserted into a facet joint to open the space for the insertion of other instruments such as the spreader, rasp, and facet fusion cage. In some embodiments, the interspinous space dilator is flexible and in other embodiments it is rigid. The dilator is configured to be slidable over the insertable guide. The dilator is capable of distending the area of the facet joint around the insertable guide to allow for better access to the spinal region.

An interspinous spreader, provides for general access to the spinal region by distracting the interspinous space. The interspinous spreader may have reverting tips to allow for greater surface area contact with the spinal region proximal to the interspinous space. In some embodiments, the interspinous spreader is not required to access a facet joint. For example, a facet joint spreader can be employed to access a facet joint in the absence of an interspinous spreader. Alternatively, a facet joint spreader is employed subsequent to the use of an interspinous spreader. The facet joint spreader is capable of rotating, and the rotation distracts the facet joint. In one embodiment, the facet joint spreader is rotated 90° thereby distracting the facet joint.

The rasp is used in decorticating the interior surface of a facet joint. Decortication is used to roughen the surface and cause bone and/or cartilage growth in response. The decortication also provides additional surface for bone graft materials, or the like, to gain a hold on the facet joint and thereby facilitate fusion of the joint. In one embodiment, the rasp is capable of sliding over the facet joint spreader prior to decorticating the facet joint.

In one aspect, a method of using the system is provided. In some embodiments, the methods include accessing a patient's spinal column; deploying the dilator; deploying the facet joint spreader comprising the distractor and the detachable distractor tip; rotating the facet joint spreader 90° relative to the deployed position of the facet joint spreader; deploying the rasp over the facet joint spreader; decorticating an interior surface of a facet joint; removing the rasp; deploying the fusion cage; disengaging the distractor tip from the fusion cage thereby positioning the fusion cage in the locked state; and moving the securement post to a secured position.

In some embodiments, such methods are conducted using an endoscopic or blinded surgical approach. In some embodiments, a paraspinal fluoro-guide is configured to guide the surgical procedures in various method steps. In some embodiments, the insertable guide facilitates the directional positioning of: the dilator; the distractor; the detachable distractor tip; the facet joint spreader; the rasp; and the fusion cage, to a facet joint. In other embodiments, the dilator; the distractor; the detachable distractor tip; the facet joint spreader; the rasp; and the fusion cage, are configured to slide over the insertable guide. In other embodiments, the facet fusion cages may be unilaterally or bilaterally inserted into the facet joints.

In another aspect, a method is provided for implementing the facet fusion system. In one embodiment, a method using the facet fusion system described above provides for facet joint fusion, thereby stabilizing or fusing adjacent cervical, thoracic, or lumbar vertebrae. In one embodiment, the method comprises: (a) accessing a patient's spinal column; (b) inserting an insertable guide; (c) dilating the area surround the insertable guide with a dilator; (d) inserting the facet joint spreader into the facet joint; (e) rotating the facet joint spreader 90° to distract the facet joint; (f) sliding a rasp over the facet joint spreader; (g) decorticating an interior surface of a facet joint with the rasp; (h) removing the rasp; (i) inserting a fusion cage attached to the tip of the distractor into the facet joint space; and (j) disengaging the distractor tip from the fusion cage thereby positioning the fusion cage in the secured state.

For the purposes of this disclosure and unless otherwise specified, "a" or "an" means "one or more". All patents, applications, references and publications cited herein are incorporated by reference in their entirety to the same extent as if they were individually incorporated by reference.

One skilled in the art will readily realize that all ranges and ratios discussed can and do necessarily also describe all subranges and subratios therein for all purposes and that all such subranges and subratios also form part and parcel of this invention. Any listed range or ratio can be easily recognized as sufficiently describing and enabling the same range or ratio being broken down into at least equal halves, thirds, quarters, fifths, tenths, etc. As a non-limiting example, each range or ratio discussed herein can be readily broken down into a lower third, middle third and upper third, etc.

All publications, patent applications, issued patents, and other documents referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed invention. Additionally the phrase "consisting essentially of" will be understood to include those elements specifically recited and those additional elements that do not materially affect the basic and novel characteristics of the claimed invention. The phrase "consisting of" excludes any element not specifically specified.

The present disclosure is not to be limited in terms of the particular embodiments described in this application. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

In addition, where features or aspects of the disclosure are described in terms of Markush groups, those skilled in the art will recognize that the disclosure is also thereby described in terms of any individual member or subgroup of members of the Markush group.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A device comprising:
a side wall having an interior surface and an exterior surface, wherein the interior surface defines an inner space and the exterior surface defines a distractor tip engagement mechanism configured to engage a facet joint distractor;
a pivot post having a pivot post axis substantially aligned with the distractor tip engagement mechanism, the pivot post secured to the interior surface of the side wall for pivoting about the pivot post axis; and
a securement post having a securement post axis extending between a first end and a second end opposite the first end, wherein the securement post is mounted to and configured to pivot about, or with, the pivot post, with the securement post axis arranged substantially orthogonal to the pivot post axis, so that the securement post is movable from an unsecured position with the first end and second end disposed within the interior space to a secured position with at least one of the first end and the second end extending beyond the exterior surface;
wherein:
the device is a facet joint fusion cage and the side wall of the facet fusion cage is flexible and is configured to flex upon receiving a pressure from the weight of a patient, so that the first and second ends of the securement post are extended through the side wall and into a facet joint of the patient by the pressure.

2. The device of claim 1, wherein at least one of the first end and second end of the securement post is pointed or burred and configured to anchor the facet fusion cage to a facet joint.

3. The device of claim 1, wherein the distractor tip engagement mechanism is configured to engage the tip of a facet joint distractor.

4. The device of claim 1, further comprising one or more anti-retropulsion spikes on the exterior surface of the facet joint fusion cage.

5. The device of claim 1, wherein in the secured position the first end and the second end are rotated in a plane substantially perpendicular to the pivot post axis by approximately 90 degrees from the unsecured position.

6. The device of claim 1, wherein the facet joint fusion cage contains a source of osteogenesis, a fusion promoting substance, a bone growth promoting material, a bone, a bone derived substances, a demineralized bone matrix, a bone graft material or bone substitute material, a mineralizing protein, a plasma spray coating, an ossifying protein, a bone morphogenetic protein, hydroxyapatite, genes coding for the production of bone, substances other than bone, or a mixture of any two or more thereof.

7. The device of claim 6, wherein the bone graft material or bone substitute material is bone graft, allograft bone, demineralized bone material, ceramic, coral, collagen/ceramic composite, bone morphogentic protein, or a combination of any two or more.

8. The device of claim 1 further comprising one or more fenestrations through the side wall.

9. The device of claim 1 wherein a portion of the pivot post extends beyond the side wall and is configured to be engaged by a tool to move the securement post from the unsecured position to the secured position.

10. A method comprising:
  providing a device, wherein the device comprises:
    a side wall having an interior surface and an exterior surface, wherein the interior surface defines an inner space and the exterior surface defines a distracter tip engagement mechanism configured to engage a facet joint distractor;
    a pivot post having a pivot post axis substantially aligned with the distractor tip engagement mechanism, the pivot post secured to the interior surface of the side wall for pivoting about the pivot post axis; and
    a securement post having a securement post axis extending between a first end and a second end opposite the first end, wherein the securement post is mounted to and configured to pivot about, or with, the pivot post, with the securement post axis arranged substantially orthogonal to the pivot post axis, so that the securement post is movable from an unsecured position with the first end and second end disposed within the interior space to a secured position with at least one of the first end and the second end extending beyond the exterior surface;
  wherein:
    the device is a facet joint fusion cage and the side wall of the facet fusion cage is flexible and is configured to flex upon receiving a pressure from the weight of a patient, so that the first and second ends of the securement post are extended through the side wall and into a facet joint of the patient by the pressure;
  positioning the facet fusion cage in a facet joint of a patient in need of a facet joint fusion; and
  pivoting the securement post from the unsecured position to the secured position wherein in the secured position one, or both, of the first end and the second end, are configured to extend beyond the side wall.

* * * * *